(12) United States Patent
Boutaghou et al.

(10) Patent No.: US 9,332,972 B2
(45) Date of Patent: May 10, 2016

(54) ASPIRATION BIOPSY APPARATUS AND METHOD

(75) Inventors: Zine-Eddine Boutaghou, North Oaks, MN (US); Peter Crane, Minneapolis, MN (US)

(73) Assignee: GREER MEDICAL, INC., Santa Barbara, CA (US)

( * ) Notice: Subject to any disclaimer, the term of this patent is extended or adjusted under 35 U.S.C. 154(b) by 957 days.

(21) Appl. No.: 13/434,526

(22) Filed: Mar. 29, 2012

(65) Prior Publication Data

US 2012/0253225 A1 Oct. 4, 2012

Related U.S. Application Data

(60) Provisional application No. 61/468,688, filed on Mar. 29, 2011.

(51) Int. Cl.
*A61B 5/00* (2006.01)
*B65D 81/00* (2006.01)
*A61B 10/02* (2006.01)

(52) U.S. Cl.
CPC ..... *A61B 10/0283* (2013.01); *A61B 2010/0208* (2013.01)

(58) Field of Classification Search
CPC . A61B 10/02; A61B 10/0233; A61B 10/0283
USPC ................. 600/562, 564, 565, 573, 576, 578
See application file for complete search history.

(56) References Cited

U.S. PATENT DOCUMENTS

| | | | | |
|---|---|---|---|---|
| 5,159,933 A | * | 11/1992 | Hut | 600/566 |
| 5,651,372 A | * | 7/1997 | Caillouette | 600/567 |
| 5,830,152 A | * | 11/1998 | Tao | A61B 10/0233 |
| | | | | 600/562 |

* cited by examiner

*Primary Examiner* — Max Hindenburg
*Assistant Examiner* — Jonathan M Foreman
(74) *Attorney, Agent, or Firm* — Billion & Armitage; Richard E. Billion

(57) ABSTRACT

An aspiration apparatus includes a barrel having a needle receiving end and a piston receiving end. The barrel has an inner diameter and an outer diameter. The piston receiving end of the barrel has substantially the same inner diameter as the inner diameter of the barrel. The barrel has an opening therein through a sidewall of the barrel. The opening is between the needle receiving end and the piston receiving end. The opening is distant from the needle receiving end. The aspiration apparatus also includes a needle sealingly attached to the needle receiving end of the barrel, and a piston having an end which substantially seals to the inner diameter of the barrel. The piston is capable of a number of positions including a first position near the needle receiving end, a third position past the opening in the barrel.

10 Claims, 16 Drawing Sheets

ASPIRATION BIOPSY APPARATUS AND METHOD

CROSS REFERENCE TO RELATED APPLICATIONS

The present application claims the benefit and priority of U.S. provisional application 61/468,688 filed Mar. 29, 2011, the disclosure of which is hereby incorporated by reference in its entirety.

TECHNICAL FIELD

Various embodiments described herein relate to an aspiration biopsy apparatus and method. More specifically, the aspiration biopsy device is capable of collecting a sample in a vacuum and releasing the vacuum after a sample is collected and before removing the needle.

BACKGROUND

Localized accumulation of excess bodily fluid in an internal region of the body frequently occurs as a result of injury, infection, surgical trauma, or some other type of damage or disorder in that internal region of the body. It is generally desirable from a medical treatment standpoint to remove such excess accumulated bodily fluid from the body to reduce swelling and pain and to promote healing. Aspiration is a procedure for removing excess accumulated bodily fluid, which employs suction to draw the bodily fluid from the body. Aspiration procedures are commonly performed on joints. A syringe is the instrument of choice for performing many types of aspirations due to its simplicity and effectiveness.

In addition to aspiration, a syringe can also be used to obtain tissue samples for analysis. The process of getting a sample is called a biopsy. A biopsy is a medical test commonly performed by a surgeon or an interventional radiologist involving sampling of cells or tissues for examination. The biopsy includes the medical removal of tissue from a living subject to determine the presence or extent of a disease. In many instances, a syringe is also the instrument of choice due to its simplicity and effectiveness.

Aspiration can be performed in any region of the body. Some parts of the body are more difficult to get to and more difficult to aspirate. It also goes without saying that different parts of the body are more sensitive to the aspiration process. The fluid can be very liquid or can be viscous.

Biopsies can be performed on growths in many parts of the body to determine if such growths are cancerous. For example, biopsies can be done on breast tissue, kidney tissue and even lung tissue. Biopsies can also be performed on cysts that may appear in many parts of the body.

In practice, the health care provider first preps the patient then inserts the needle of the syringe into the afflicted area. The plunger of the syringe is manually pulled backward, displacing the plunger within the barrel of the syringe to create a suction. The suction draws the accumulated bodily fluid from the from into the barrel of the syringe. When the barrel is filled, the health care provider withdraws the needle from the patient and disposes the aspirated bodily fluid in a sanitary manner, for example, by emptying the aspirated bodily fluid from the syringe into a disposal reservoir. It is oftentimes also desirable to retain samples of the aspirated bodily fluid for future diagnostic purposes.

The procedure for performing a biopsy, in many instances, is very similar to the practice of aspirating an area. The health care provider preps the patient then inserts the needle of the syringe into the area from which a sample is to be obtained. The plunger of the syringe is manually pulled backward, displacing the plunger within the barrel of the syringe to create a suction. The suction draws the sample into the barrel of the syringe. The sample can then be provided to a pathologist for further analysis.

Some of these procedures require more power than others. For example, obtaining bone marrow for either a transplant or for analysis is one of the procedures which requires more muscle power than other procedures. When a health care professional applies "muscle" to accomplish the job, it can become difficult to keep the syringe steady. Thus, more effort is required of a health care professional, there is increased discomfort for the patient, and the resulting sample may be less than ideal.

In many operations for obtaining a sample, a vacuum is used to collect the sample. The vacuum is maintained as the needle is removed from the sample area. When this occurs, there is also a possibility that the collection device may obtain a portion of a sample from other than the effected area.

SUMMARY OF THE DESCRIBED EMBODIMENTS

An aspiration apparatus includes a barrel having a needle receiving end and a piston receiving end. The barrel has an inner diameter and an outer diameter. The piston receiving end of the barrel has substantially the same inner diameter as the inner diameter of the barrel. The barrel has an opening therein through a sidewall of the barrel. The opening is at a position of the opening is between the needle receiving end and the piston receiving end. The opening is distant from the needle receiving end. The aspiration apparatus also includes a needle sealingly attached to the needle receiving end of the barrel, and a piston having an end which substantially seals to the inner diameter of the barrel. The piston is capable of a number of positions including a first position near the needle receiving end, a third position past the opening in the barrel. Moving the piston away from the first position results in a vacuum being formed within the barrel, and moving the piston to a third position past the opening in the barrel releases the vacuum. The opening or hole in the barrel acts as a vent or port to allow the inner portion of the barrel to equilibrate to atmospheric pressure. The barrel includes a pair of finger holds. The piston includes an enlarged end opposite the seal end. In one embodiment, the aspiration apparatus further includes a mechanical apparatus to controllably move the piston between a first position and a second position. The mechanical apparatus also controllably moves the piston to a third position. The mechanical apparatus includes an inner sleeve removably attached to the piston, and an outer sleeve capturing the barrel, the outer sleeve including a lever to enable moving of the inner sleeve and attached piston with respect to the outer sleeve.

The aspiration apparatus also includes a spring positioned between the inner sleeve and the outer sleeve. The inner sleeve has an inner shoulder for receiving one end of the spring and the outer sleeve includes an outer shoulder for receiving the other end of the spring. The spring used can be one of many types of coil springs. In one embodiment, the spring has closed ends. In another embodiment the spring has a closed and boxed end. The inner sleeve is attached to the piston and moves with the piston. The inner sleeve includes a primary latching surface. The outer sleeve is attached to the barrel. The outer sleeve includes a lever rotatably attached to the outer sleeve and having a primary latch hook for holding the inner sleeve in a position where the piston is in a first position with respect to the barrel. In the first position the sealing end of the piston is position near the needle end of the barrel.

In another embodiment of the aspiration apparatus, the inner sleeve is attached to the piston and moves with the piston. The inner sleeve includes a primary latching surface and a secondary latching surface. The outer sleeve is attached to the barrel. The outer sleeve includes a first lever rotatably attached to the outer sleeve. The outer sleeve also has a primary latch hook for holding the inner sleeve in a position where the piston is in a first position with respect to the barrel. The outer sleeve also includes a second lever for latching the secondary latching surface to hold the piston at a position with respect to the barrel intermediate the first and third position. In one embodiment, the first lever and the second lever are rotatably attached to the same axis. In still another embodiment, the first lever and the second lever rotate about the same axis.

A method of collecting biopsy samples includes positioning an end of a needle into an area where a sample is collected, placing a vacuum on the needle to collect a sample in the area of the end of the needle, releasing the vacuum after the sample has been collected, removing the needle from the area where the sample was collected.

BRIEF DESCRIPTION OF THE DRAWINGS

The embodiments will be readily understood by the following detailed description in conjunction with the accompanying drawings, wherein like reference numerals designate like structural elements, and in which.

DETAILED DESCRIPTION

In the following paper, numerous specific details are set forth to provide a thorough understanding of the concepts underlying the described embodiments. It will be apparent, however, to one skilled in the art that the described embodiments may be practiced without some or all of these specific details. In other instances, well known process steps have not been described in detail in order to avoid unnecessarily obscuring the underlying concepts.

Figure 1:
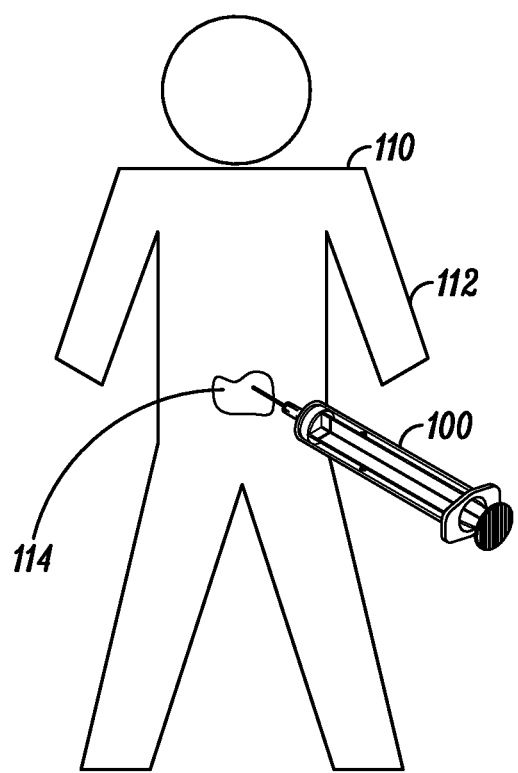
FIG. 1 is a view of an aspiration apparatus during a biopsy or aspiration, according to an embodiment of the invention.

FIG. 1 is a view of an aspiration apparatus 100 during a biopsy or aspiration, according to an example embodiment. The aspiration apparatus 100 includes a needle 110 and a vacuum source 112. The needle is moved to a position within a tumor, growth, or other sample site 114 from where a sample is to be collected. The vacuum source 112 is enabled while the needle 110 is positioned at the sample site 114. The needle can be moved through the sample site 114. When the operator feels that a sufficient sample has been collected, the vacuum source 112 is disabled and the aspiration apparatus is removed from the sample site 114 and from the subject.

Figure 2:
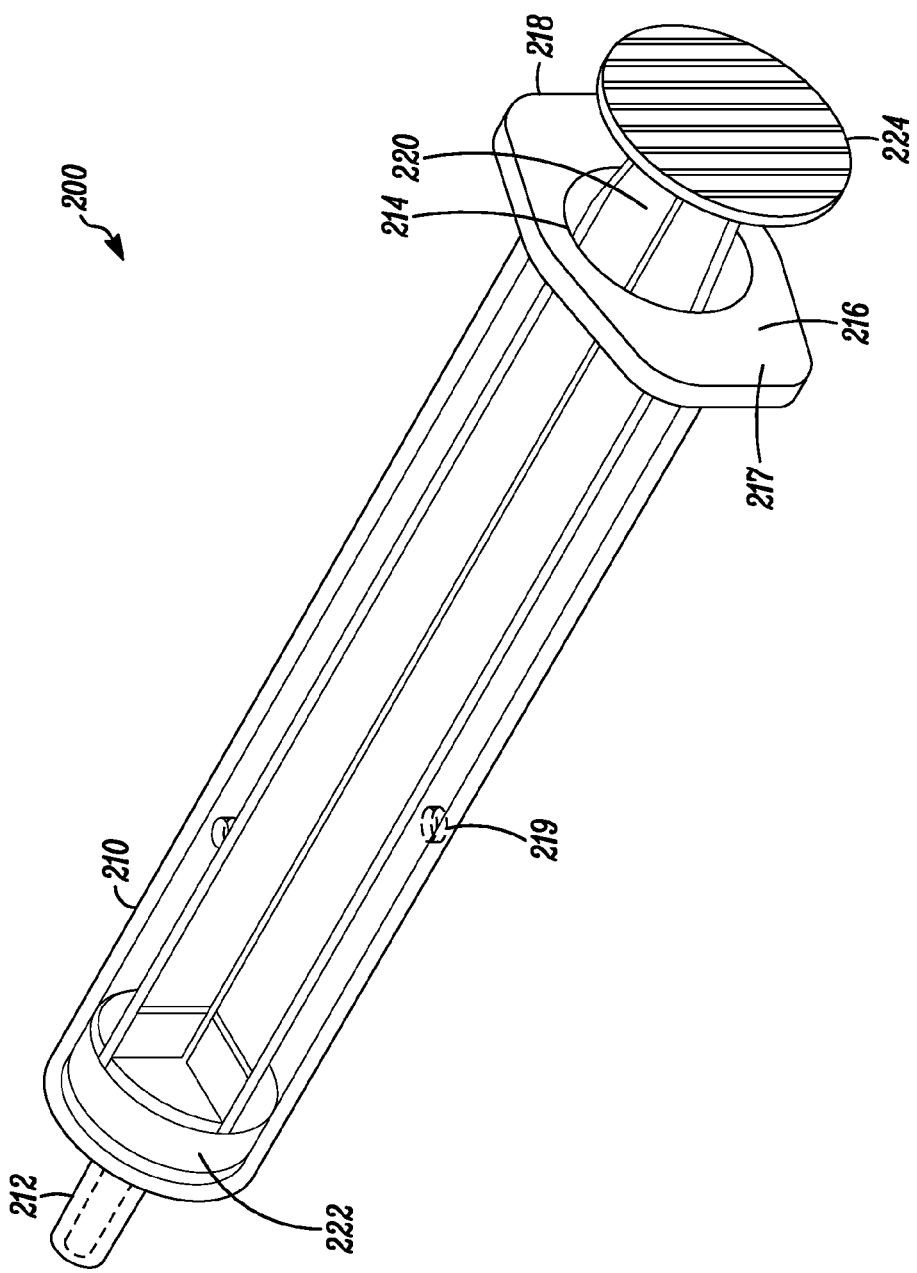
FIG. 2 is a perspective view of an aspiration apparatus, according to an example embodiment. (modify syringe)

FIG. 2 is a perspective view of an aspiration apparatus 200, according to an example embodiment. The aspiration apparatus or biopsy device 200 includes a barrel 210 and a plunger or piston 220. The barrel 210 includes a needle receiving end 212 and a piston receiving end 214. At or near the piston receiving end 214 is a finger rest 216. The finger rest 216 includes a first tab and a second tab 217 and 218, respectively. The barrel 210 also includes an opening 219 which is positioned between the needle receiving end 212 and the piston receiving end 214. The opening 219 is referred to as a port or vent. The piston 220 has a sealing end 222 and an enlarged end 224. The sealing end 222 includes a rubber gasket or the like which seals the end 222 to the inner diameter of the barrel 210. When the piston 220 is in the position shown in FIG. 2, there is no vacuum formed by the aspiration device 200. When the piston 220 is drawn back using the enlarged end 224, a vacuum is formed in the chamber formed between the sealed end 222 and the needle receiving end 212. The vacuum is increased as the piston 220 is drawn back further. When the piston 220 is drawn back beyond the opening 219 in the barrel 210, the vacuum is released and the pressure inside the chamber equilibrate with the atmospheric pressure outside the chamber. The opening 219 serves as a vent or port to release or relieve the vacuum formed on the inside of the barrel 210 as the piston 220 is drawn back from the needle receiving end 212.

In operation, a needle attached to the needle receiving end 212 is positioned at a sample collection site 114 within a body or subject. As the needle is being positioned at the sample collection site 114, the piston 220 is positioned near the needle receiving end 212. In other words, as the needle is positioned there is no vacuum formed which could draw tissue or fluids into the barrel 210. Once the needle is correctly position at the sample collection site 114, the plunger or piston 220 is drawn back from the needle receiving end 212 to produce a vacuum within the barrel 210. The needle can then be moved through the sample site 114 to collect the sample. During sample collection times it is necessary to have a vacuum on the needle in order to properly can collect the sample. Once the sample is collected the plunger or piston 220 is drawn further back from the needle receiving end 212 until the plunger or piston 220 passes the vent or port opening 219. Once the sealing portion 222 is past the opening 219, the vacuum formed between the sealing end 222 and the barrel 210 is released or relieved. After the vacuum has been released, the needle is removed from the collection site and the body. Because there is no vacuum, there will be little if any fluid or tissue collected from the subject that is not from the sample site 114. In one example embodiment, the aspiration apparatus 100 is a syringe available from B-D of Franklin Lakes, N.J., USA. The syringe is modified in that at least one opening 219 is placed in the barrel 210 of the syringe body. In some embodiments, more than one opening is made. The opening is for releasing a vacuum produced within the barrel.

Figure 3:
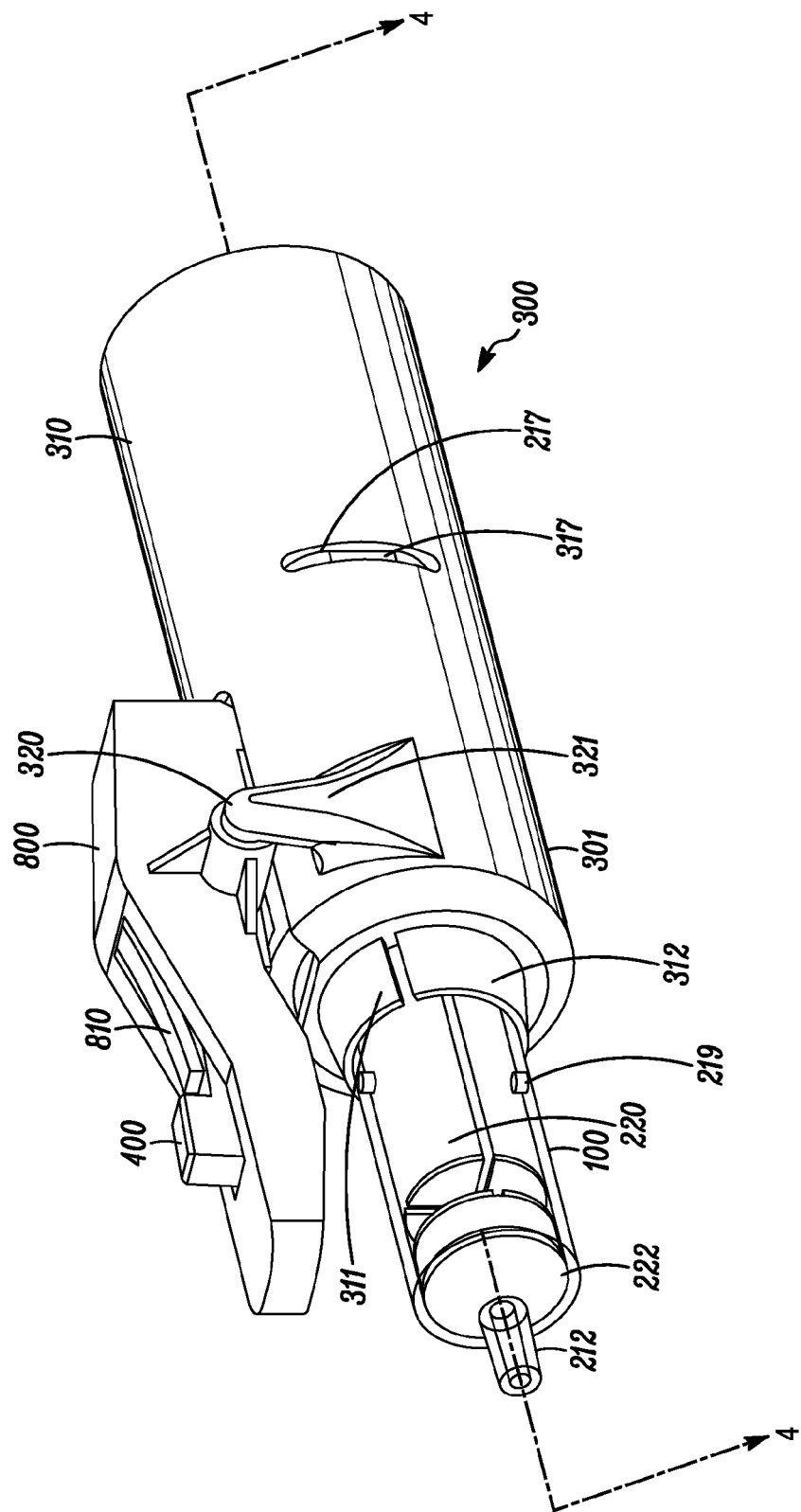
FIG. 3 is a perspective view of another embodiment of an aspiration apparatus having a mechanical portion attached thereto, according to an example embodiment.

FIG. 3 is a perspective view of another embodiment of an aspiration apparatus 300, according to an example embodiment. The aspiration apparatus 300 includes an aspiration apparatus 100 and a mechanical portion 301. The mechanical portion 301 fits over the aspiration apparatus 100. Shown in FIG. 3, is an outer sleeve 310. The outer sleeve includes a pair of slits or slots for receiving the finger rests 217 and 218 of the aspiration apparatus 100. As shown in FIG. 3, there is only one slot 317 shown and it captures finger rest 217. Mechanical portion 301 also includes a set of barrel captures, which include barrel capture 311, 312. Attached to the main body or outer sleeve 310 of the mechanical portion 301 is an axle 320. The axle is held off the main body or outer sleeve 310 by stanchions (one of which is shown) 321, 322. Rotatably attached to the axle 320 is a button lever 800 and a secondary button lever 400. The button lever 800 includes a torsion spring 810 which places a force on the secondary button lever 400. The mechanical portion 301 provides a mechanical aid to make the aspiration device 300 easier to handle than an aspiration device such as aspiration device 100. Mechanical portion 301 holds the sealing end 222 of the plunger or piston 220 and a first position near the needle receiving end 212. Mechanical portion 301 moves the plunger or piston to a second position where a vacuum is formed within the barrel 210 and also moves the plunger or piston 220 to a position where the vacuum is released.

Figure 4:
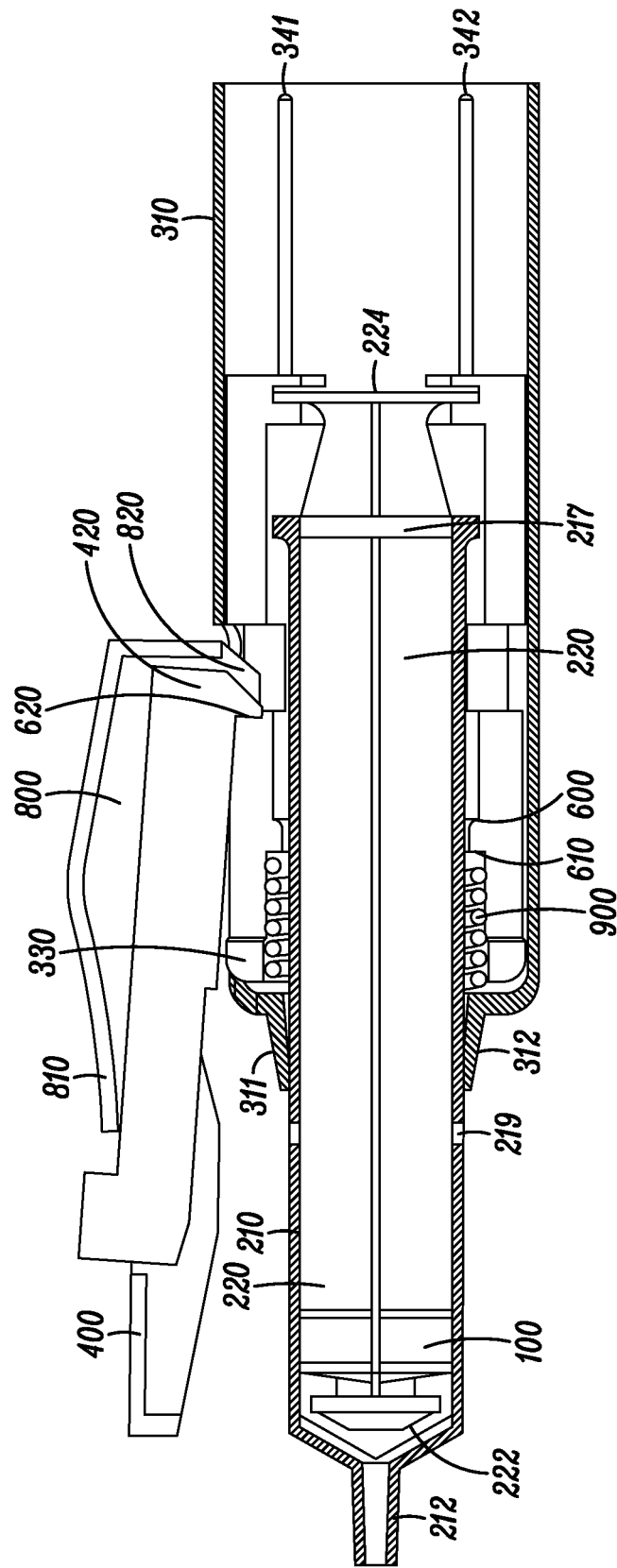
FIG. 4 is a cross-sectional view along cut line 4-4 of the aspiration apparatus having a mechanical portion attached thereto, according to an example embodiment.

FIG. 4 is a cross-sectional view along cut line 4-4 of the aspiration apparatus 300 having a mechanical portion 301 attached thereto, according to an example embodiment. Mechanical portion 301, in addition to having an outer sleeve 310, also includes an inner sleeve 600. The inner sleeve includes one and that captures the plunger or piston 220. More specifically the inner sleeve 600 captures the enlarged and 224 of the piston 220. The other end of that the inner sleeve 600 fits over the exterior surface of the barrel 210. The other end is capable of sliding over the barrel 210. The inner sleeve 600 also includes an inner shoulder 610. The outer sleeve 310 also includes an outer shoulder 330. Mechanical portion 301 also includes a spring 900 which fits over the barrel 210 and underneath the inner sleeve 600. One end of the spring 900 abuts the inner shoulder 610 and the other end of the spring 900 abuts the outer shoulder 330. The spring 900, as shown in FIG. 4, is compressed when the plunger or piston 220 is in a first position that corresponds to the plunger or piston 220 being fully inserted into the barrel 210.

As shown in FIG. 4 the primary button lever 800 includes a hook latch 820. The secondary button lever 400 also includes a hook latch 420. The hook latch 820 and the hook latch 420 latch to a primary latching surface 620 of the inner sleeve 600. When the hook latch 820 and the hook latch 420 are positioned on the primary latching surface 620, the plunger piston 220 is held in the position where it is substantially fully inserted into the barrel 210. In this position, the spring 900 is compressed and produces a spring force on the inner shoulder 610 and on the outer shoulder 330. The latch 820 of the primary button lever 800 holds the inner sleeve in position with respect to the outer sleeve 310. Also included in FIG. 4, are a first guide rail and a second guide rail 341, 342 which are shown on the interior surface of the outer sleeve 310. Only half of the outer shell 310 is shown in this cutaway view, so there are two other guide rails not shown. The guide rails, such as guide rails 341, 342 are for controlling the movement of the finger rests 217, 218 of the barrel portion 210. The guide rails act as stops or brackets to limit the movement of the individual finger rests 217, 218 during assembly of the mechanical portion 301 with the aspiration apparatus 100.

Figure 5:
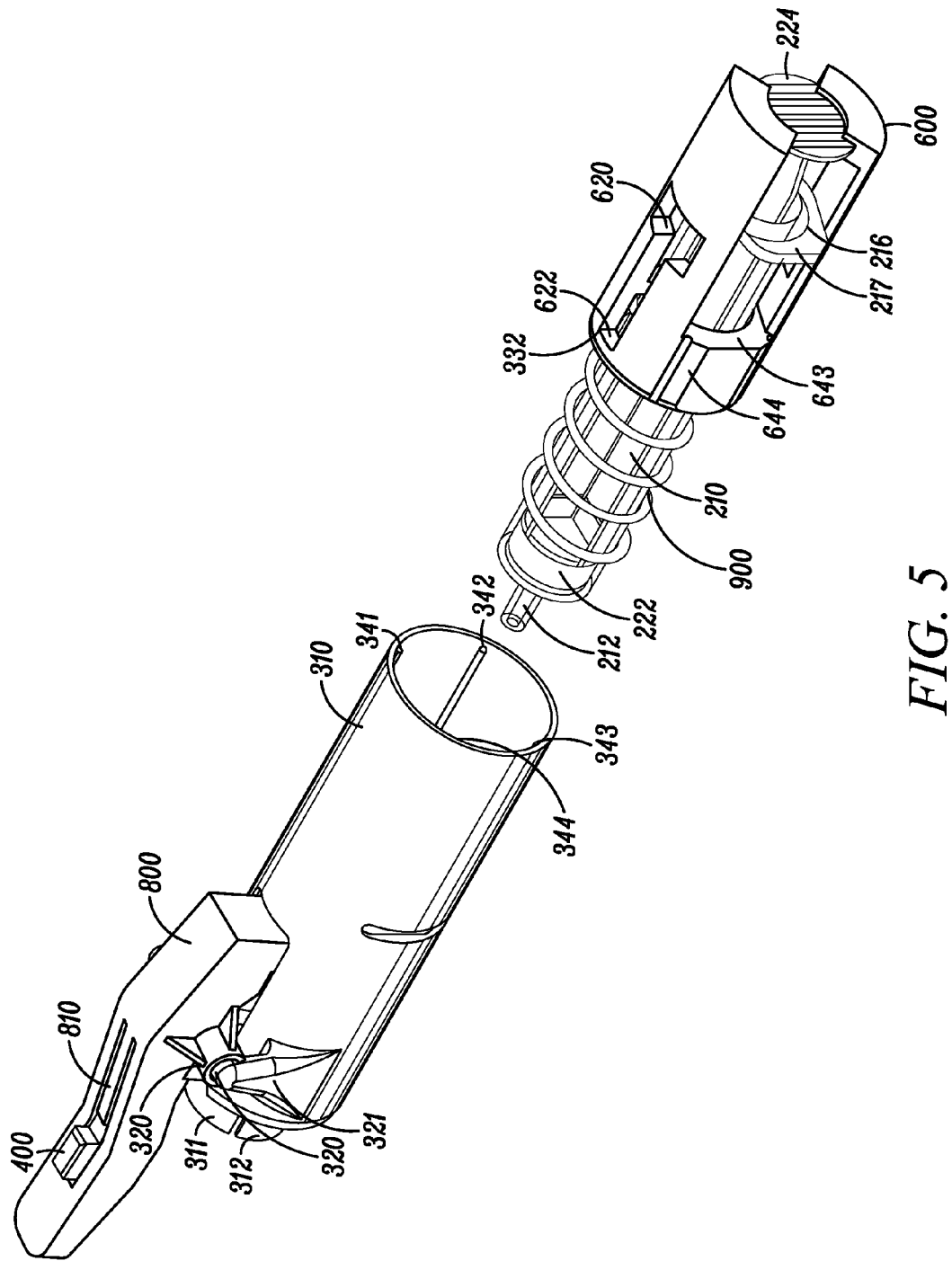
FIG. 5 is an exploded view of the aspiration apparatus having a mechanical portion, according to an example embodiment.

FIG. 5 is an exploded view of the aspiration apparatus 300 having a mechanical portion 301, according to an example embodiment. In the exploded view of the aspiration apparatus 300 the spring 900 is fully extended and is writing over the top of the exterior of the barrel 210 of the aspiration apparatus 100. Also shown are the guide rails 341, 342, 343, 344 on the interior surface of the outer sleeve 310. The inner sleeve also includes a set of channels which correspond to the guide rails 341, 342, 343, 344. Shown are channels 644, 643. The channels engage the guide rails 341, 342, 343, 344 during assembly of the aspiration apparatus 300. It should be noted that the latches 420 and 820 include a surface that will allow the latch to ride over the inner sleeve 600 as it is being inserted into the outer sleeve 310. During initial assembly the inner sleeve 600 is attached to the aspiration device 100 and as shown in FIG. 5 is inserted into the outer sleeve 310 and through the barrel captures 311, 312. Fully inserting the inner sleeve 600 compresses the spring and causes the primary button latch 800 and specifically the latch 820 associated there with, to latch the primary latching surface 620 of the inner sleeve. Basically, when fully assembled the device 300 appears as it does in FIGS. 3 and 4.

Figure 6:
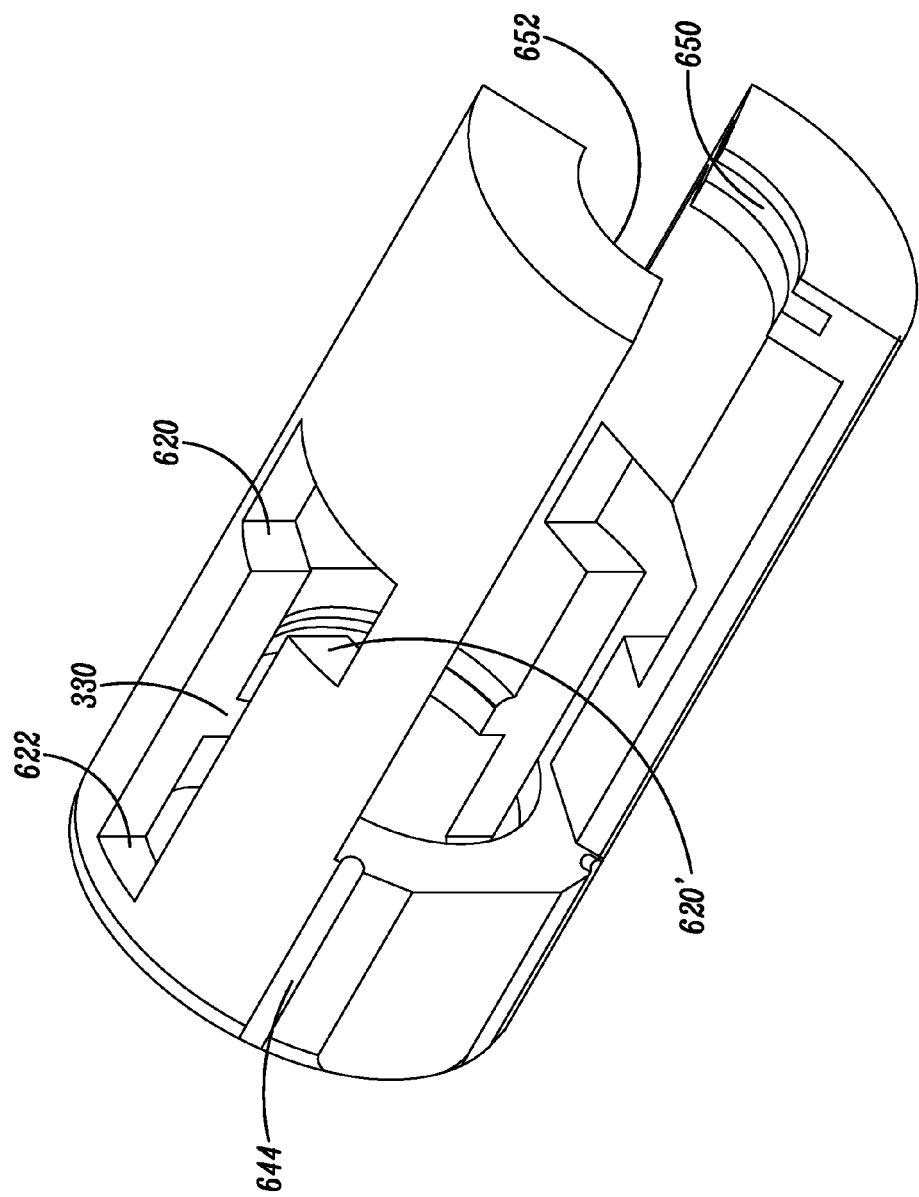
FIG. 6 is a perspective view of the inner sleeve of the mechanical portion of the aspiration apparatus, according to another example embodiment.

FIG. 6 is a perspective view of the inner sleeve 600 of the mechanical portion 301 of the aspiration apparatus 300, according to another example embodiment. The inner sleeve 600 includes the primary latching surfaces 620 and 620' Inner sleeve also includes a secondary latching surface 622. The openings near the latch the primary latching surfaces 620, 620' accommodate the latch hooks 820, 420. The open area between the primary latching surfaces 620, 620' and the secondary latching surface 622 accommodates the latch hook 420 associated with the secondary button latch 400. The distance between the latching surfaces 620, 620' and the latching surface 622 is of a length that corresponds to withdrawing the plunger or piston 220 out of the barrel 210 to a position where there is still a vacuum produced within the barrel 210. The inner sleeve 600 is made so that they can be inserted in either of two directions and function properly in both orientations. As a result there is a similar shape slot with primary latching surfaces and a secondary latching surface on the other half or bottom half of the inner sleeve 600. The channel 644 is one of four channels that engage the guide rails 344, 343, 341, 342. Inner sleeve also includes piston capture devices 650 and 652. The piston capture devices 650, 652 are channels dimensioned to receive the enlarged end 224 (shown in FIG. 5). The region near the capture devices 650, 652 is made of a flexible material to allow the capture devices to be moved outwardly over the enlarged end 224 of the piston 220.

Figure 7:
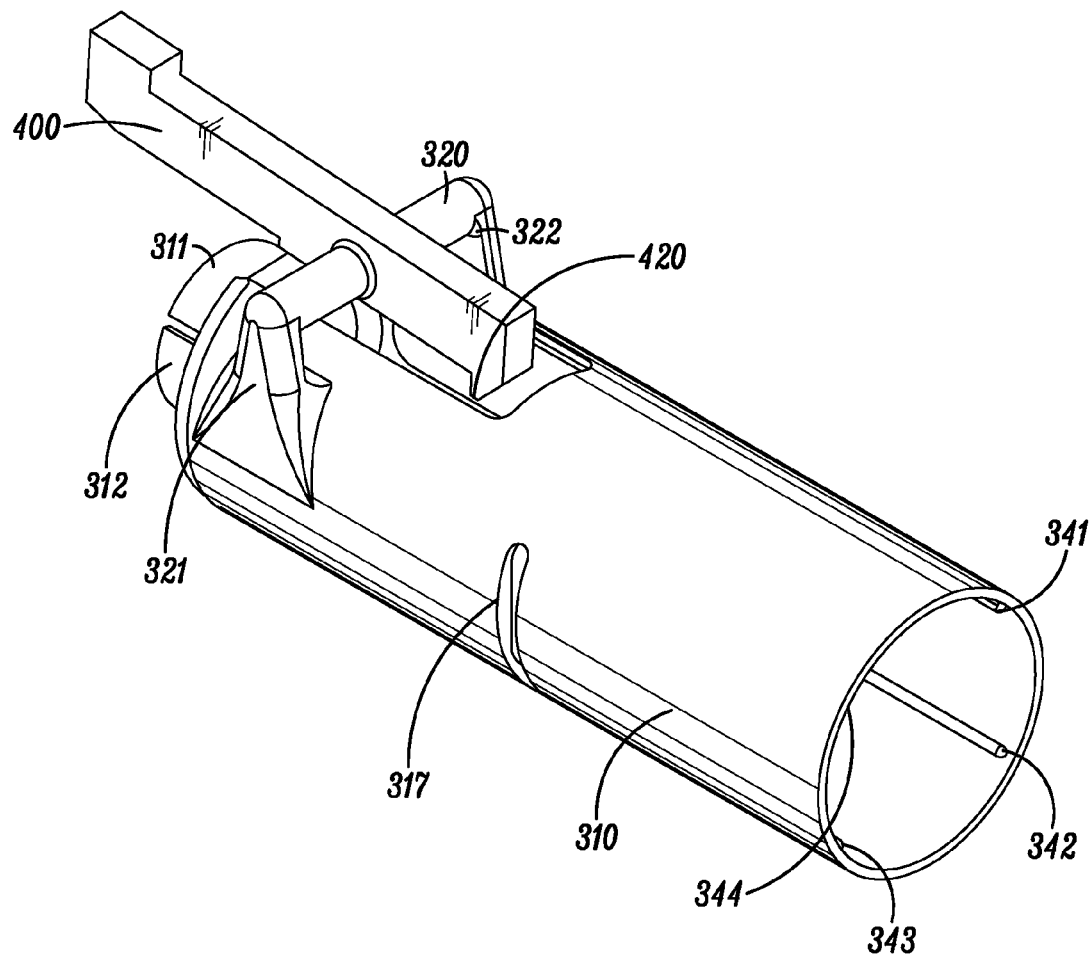
FIG. 7 is a perspective view of the outer sleeve of the mechanical portion of the aspiration apparatus, according to another example embodiment.

FIG. 7 is a perspective view of the outer sleeve 310 of the mechanical portion 301 of the aspiration apparatus 300, according to another example embodiment. The axle 320 is attached to stanchions 321, 322. The stanchions are attached to the exterior of the outer shell 310. The secondary button latch 400 is rotatably attached to the axle 320. The body of the outer shell 310 also includes slots or slits 317 which are also known as finger rest capture slots. The finger rest capture slots 317 are dimensioned to receive the finger rests 217, 218 of the barrel portion 210 of the aspiration apparatus 100. The body of the outer shell 310 is made of a flexible plastic so that the outer surface of the outer shell 310 can be temporarily deformed to produce an oval cross-section as the finger rests 217, 218 are being inserted into the finger rest capture slots 317, 318 (not shown).

Figure 8:
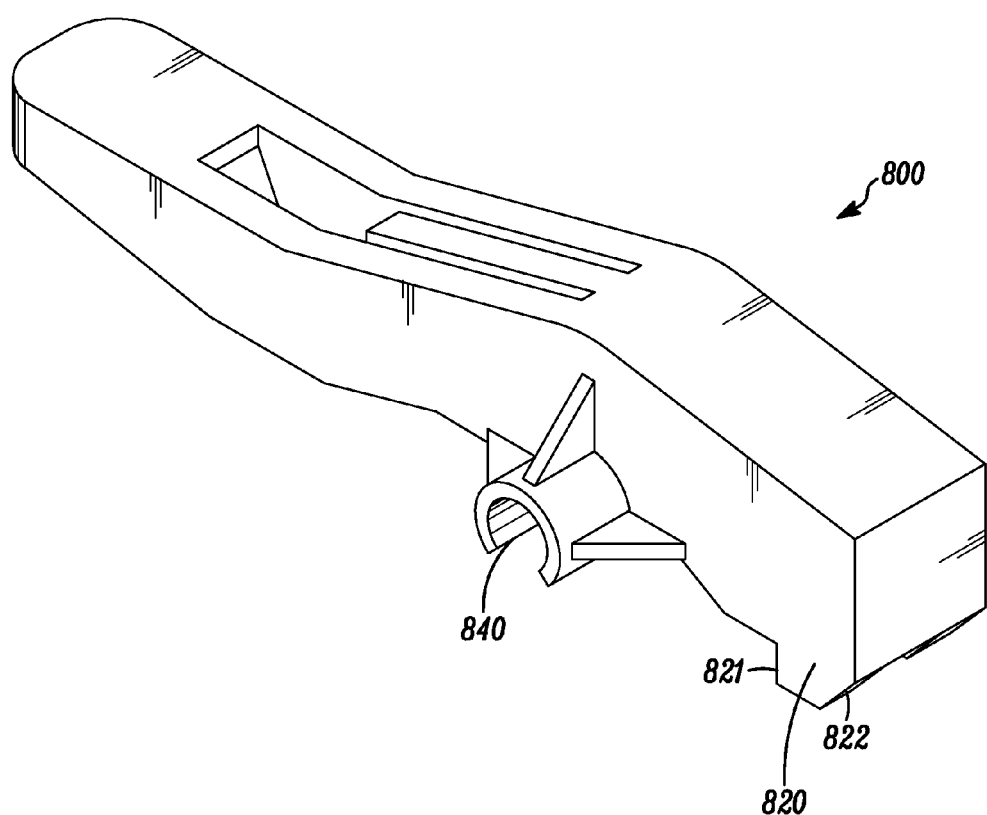
FIG. 8 is a perspective view of the button lever of the mechanical portion of the aspiration apparatus, according to another example embodiment.

FIG. 8 is a perspective view of the button lever 800 of the mechanical portion 301 of the aspiration apparatus 300, according to another example embodiment. The primary button lever 800 includes the latch hook 820. The latch hook 820 includes a latching surface 821 and a cam surface 822 which allows the latch to pass through an opening near the primary latching surface 620 of the inner sleeve 600 (shown in FIG. 4). The primary button lever 800 also includes an axle capture 840. The axle capture 840 is made of flexible material so that it can flex and pass over the axle 320 of the outer sleeve 310. There are actually two axle capture devices. The axle capture device 840 is split so that the primary button lever 800 fits over the secondary button lever 400. The secondary button lever 400 is already attached to the axle 320 when the primary button lever 800 is attached to the axle 320. The second axle capture portion is not shown in FIG. 8.

Figure 9:
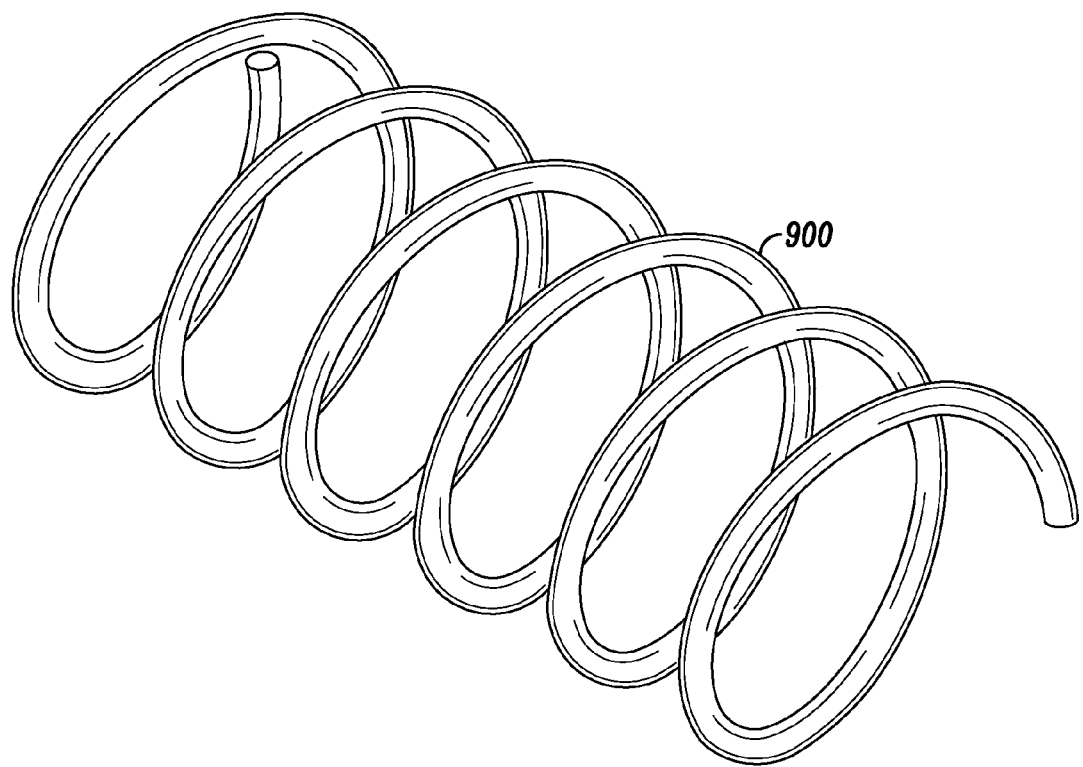
FIG. 9 is a perspective view of a spring of the mechanical portion of the aspiration apparatus, according to another example embodiment.

FIG. 9 is a perspective view of a spring 900 of the mechanical portion 301 of the aspiration apparatus 300, according to another example embodiment. The spring as an inner diameter which is slightly larger than the outer diameter of the barrel 210 of the aspiration apparatus 100. The spring 900 shown as open ends. It is contemplated that a spring with closed and squared ends could be used in the mechanical portion 301. The spring needs to produce enough force or have a spring constant that will produce a force over a length of the stroke of the piston 220 between a first position where the piston is substantially fully inserted into the barrel 210 and a third position where the sealing end 222 of the piston is beyond the opening 219 in the barrel 210.

Figure 10:
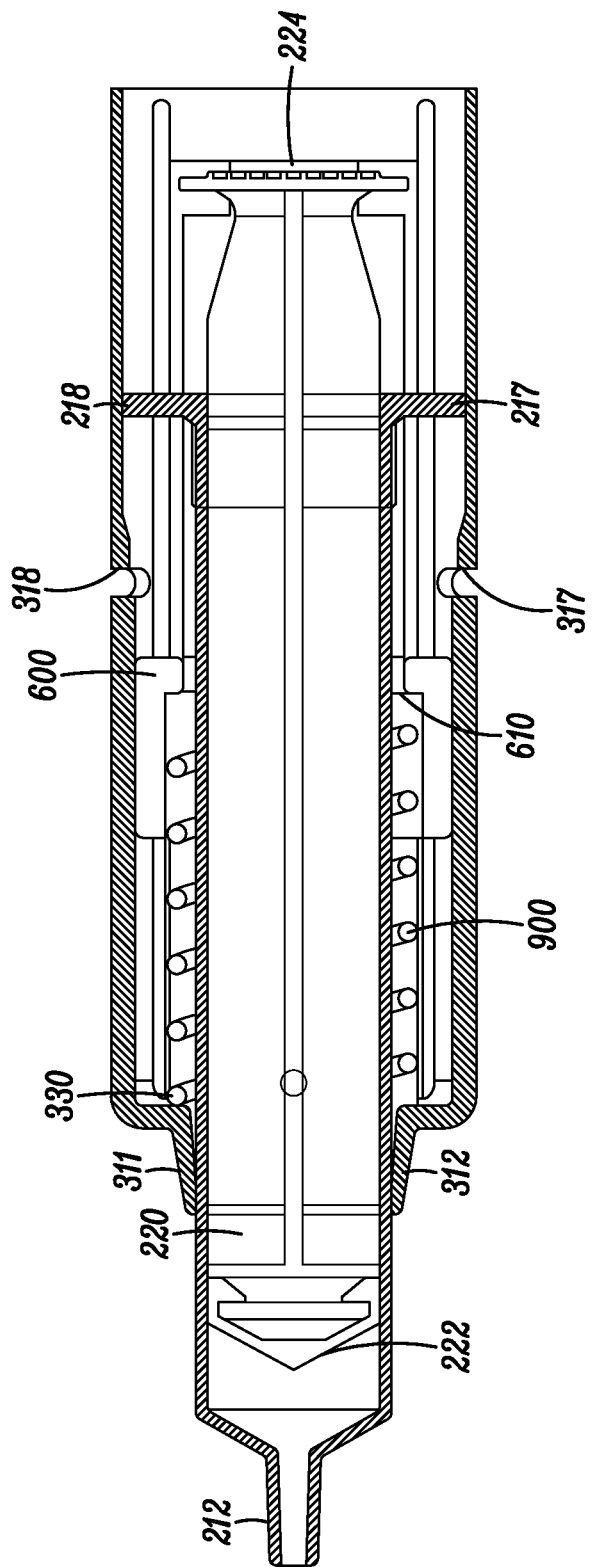
FIG. 10 is a cross-sectional view of the aspiration apparatus having a mechanical portion attached thereto as it is being assembled, according to an example embodiment.

FIG. 10 is a cross-sectional view of the aspiration apparatus 300 having a mechanical portion 301 attached thereto as it is being assembled, according to an example embodiment. The first step in the assembly is shown in FIG. 5 above. The remaining steps of the assembly are discussed in FIGS. 10 through 13. In FIG. 5, the inner sleeve 600, the spring 900 and the aspiration device 100 have been assembled and are about to be inserted into the outer sleeve 310. As shown in FIG. 10, the inner sleeve 600, the spring, and the aspiration device 100 have been inserted into the outer sleeve 301 so that the end of the barrel 210 is captured in the barrel capture device 311, 312 and so that the ends of the spring 900 of but the outer shoulder 330 of the outer shell 310, and the inner shoulder 610 of the inner sleeve 600. As shown, the sealing end 222 of the piston 220 is still a distance away from the needle retaining end 212 of the barrel 210.

Figure 11:
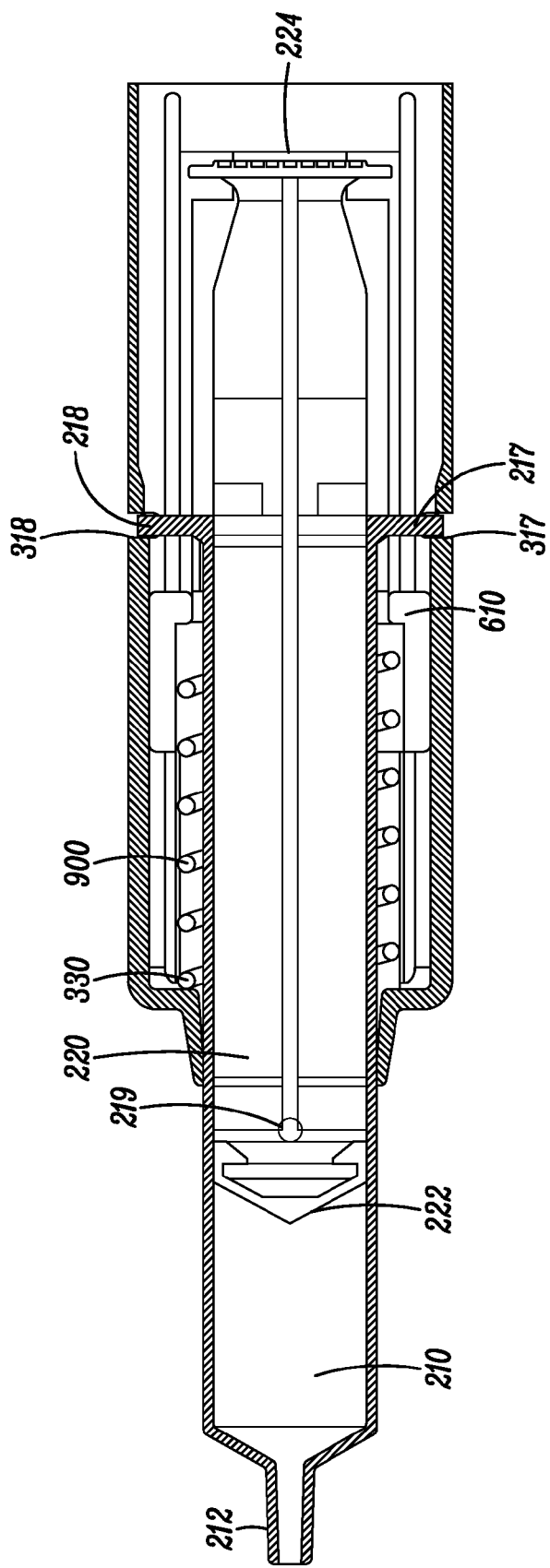
FIG. 11 is a cross-sectional view of the aspiration apparatus having a mechanical portion attached thereto as it is being assembled, according to an example embodiment.

FIG. 11 is a cross-sectional view of the aspiration apparatus having a mechanical portion attached thereto as it is being assembled, according to an example embodiment. The inner sleeve 600, aspiration device and the spring 900 are inserted into the outer sleeve 310 until the finger rests 217 and 218 are inserted into the finger rest captures 317 and 318, respectively. In one embodiment, tooling is need to squeeze the outer sleeve 310 to allow separation between the finger rest captures 317, 318 so that the actual finger rests 217, 218 can be inserted therein. From this point forward the plunger or piston is inserted further into the barrel 210 to a position where the primary button lever 800 laches to the primary latch surface 620 of the inner sleeve 600. At this position, the spring 900 is compressed more fully.

Figure 12:
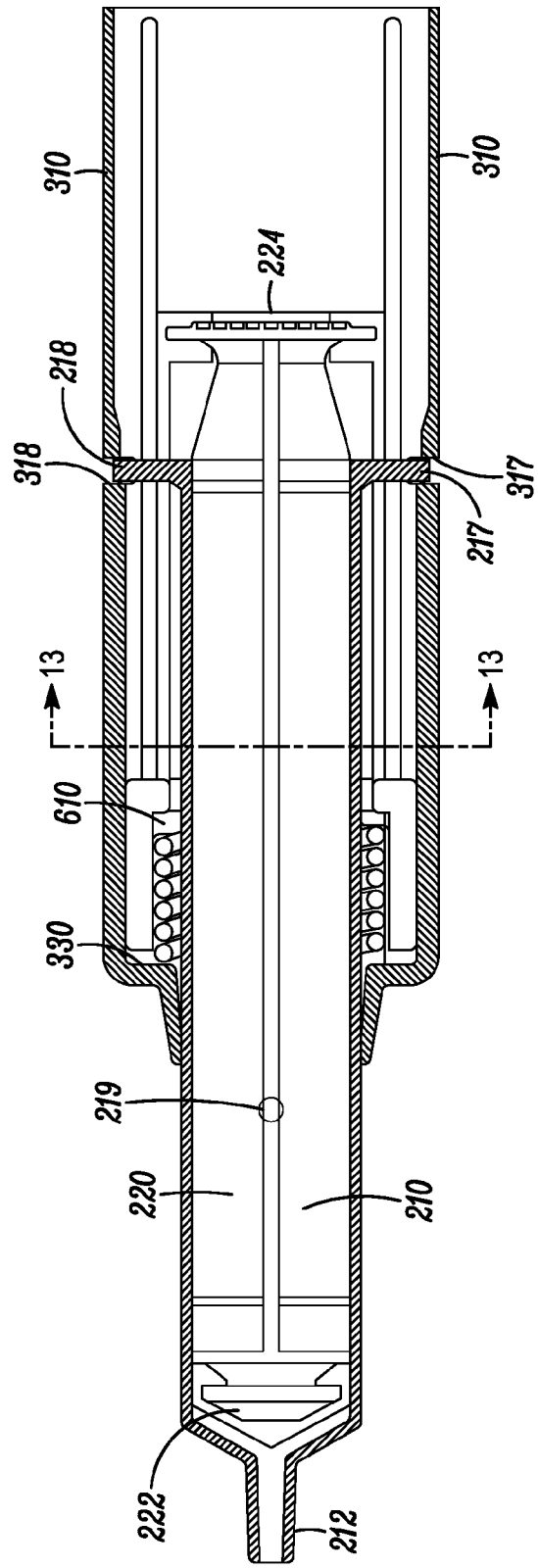
FIG. 12 is a cross-sectional view of the aspiration apparatus having a mechanical portion attached thereto as it is being assembled and after the finger rests of the syringe engage the finger rest slots in the outer sleeve, according to an example embodiment.

FIG. 12 is a cross-sectional view of the aspiration apparatus 300 having a mechanical portion 301 attached thereto as it is being assembled and after the finger rests 217, 218 of the syringe or aspiration apparatus 100 engage the finger rest slots 317, 318 in the outer sleeve 300, according to an example embodiment. The plunger piston 220 is shown substantially fully inserted into the barrel 210 of the aspiration apparatus 100. In this position the primary button latch 800 and more specifically the hook 820 is hooked to the primary latch surface 620 of the inner sleeve 600. The spring 900 is fully compressed and placing a spring force on the inside shoulder 610 of the inner sleeve 600 and on the outside shoulder 330 of the outer sleeve 310

Figure 13:
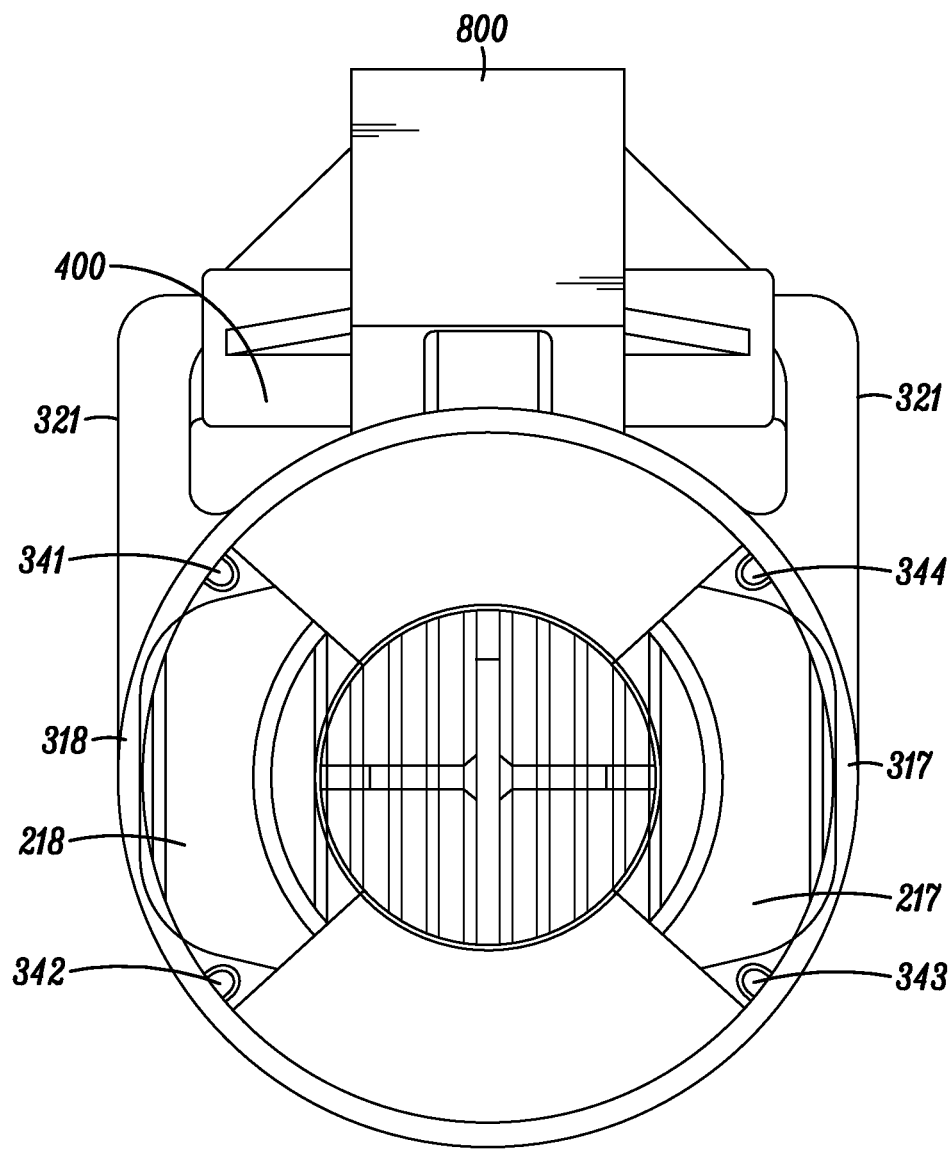
FIG. 13 is a cross-sectional view of the assembled aspiration apparatus along cut line 13-13 in FIG. 12, according to an example embodiment.

FIG. 13 is a cross-sectional view of meaning screen the assembled aspiration apparatus along cut line 13-13 of FIG. 12, according to an example embodiment. FIG. 13, the primary button latch 800 and the secondary button latch 400 are latched to the primary latch surface 620 of the inner sleeve. In addition, the finger rest 217 and 218 are captured by the finger rest captures 317, 318 respectively. Should also be noted that the finger rests 217, 218 are limited in motion by guide rails 341, 342, 343, 344. Guide rails 341 and 342 guide finger rest 218. Guide rails 343 and 344 guide finger rest 217. As mentioned previously, the guide rails 341, 342, 343, 344 also guide the inner sleeve 600 that has corresponding channels in its exterior surface during assembly and use of the mechanical portion 301.

Now referring to FIGS. 4, 14 and 15, the operation of the aspiration apparatus 300 will be discussed. FIG. 4 is a cross-sectional view of the aspiration apparatus 300 with the primary button lever latch 820 latch to the primary latch surface 620 of the inner sleeve 600. This is the position of the aspiration apparatus 300 when it is about to be used to gather a sample or do a biopsy on a subject. In this position, the plunger or piston 220 is fully inserted into the barrel 210 and no vacuum is being produced. When in this position, the aspiration device is moved to the sample collection area or zone 114. Since no vacuum is being applied to the needle 110 (shown in FIG. 1), no sample or very little other tissue will be pulled into the needle. While in this position, the needle is positioned at the target or sample collection area or zone 114.

Figure 14:
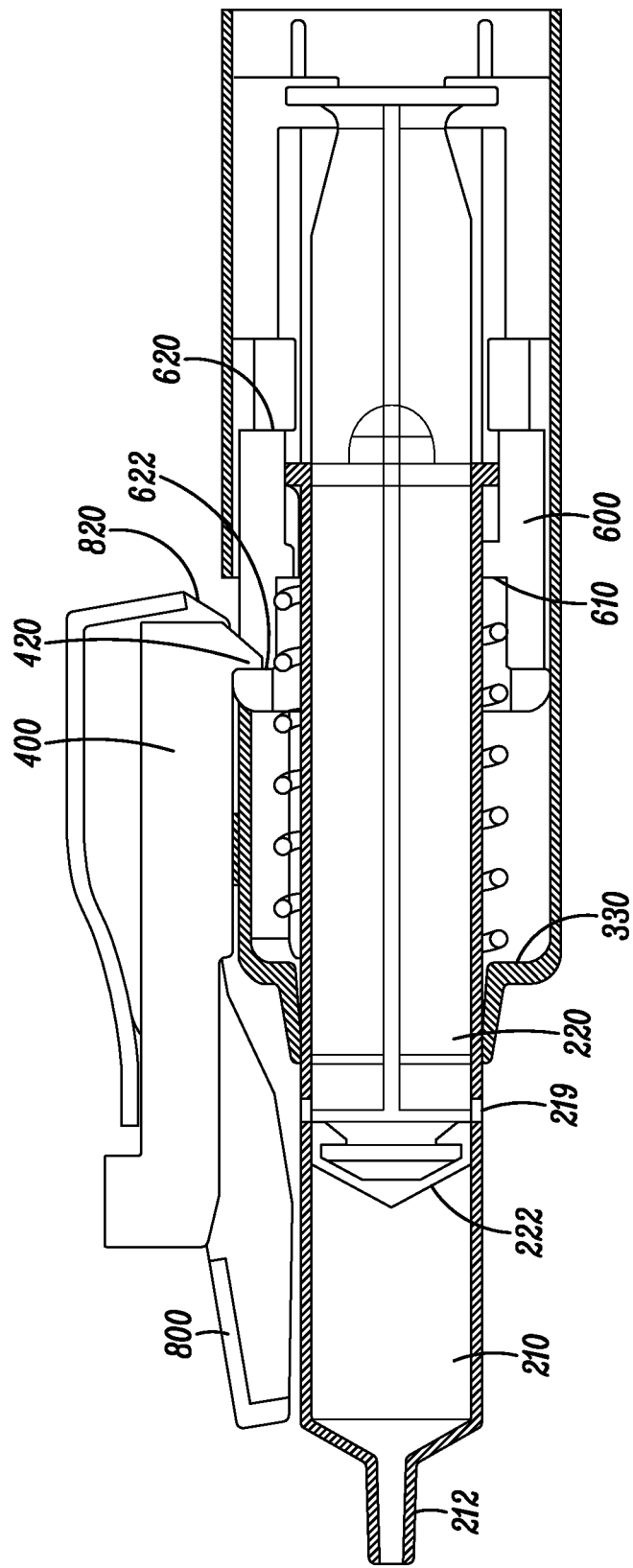
FIG. 14 is a cross-sectional view of the aspiration apparatus with the second latch hook of the second latch engaging the second latch engaging surface of the inner sleeve, according to an example embodiment.

FIG. 14 is a cross-sectional view of the aspiration apparatus with the second latch hook of the second latch engaging the second latch engaging surface of the inner sleeve, according to an example embodiment. The primary button latch 800 is depressed to remove the latch hook 820 from the primary latching surface 620 of the inner sleeve 600. When unlatched, the spring 900 forces the inner sleeve 600 away from the needle retaining end 212 of the barrel 210. The plunger or piston 220 moves backward and causes a vacuum in the chamber between the needle retaining end 212 and the sealing end 222 of the piston 220. The hook 420 of the secondary latch 400 engages the secondary latch surface 622 of the inner sleeve 600. The distance moved is just the amount of distance the can be allowed in still pull a vacuum in the chamber. As shown in FIG. 14, the sealing end 222 is close to the opening or mentor port 219 in the sidewall of the barrel 210. At this position, a vacuum is produced by the aspiration apparatus 300. Also all of the aspiration apparatus 300 is in this position, the needle 110 is moved through the sample area 114 to collect the sample. The needle is moved through the sample area while there is a vacuum present. This provides the maximum possibility that a sample will be obtained from the target or sample area 114 (shown in FIG. 1).

Figure 15:
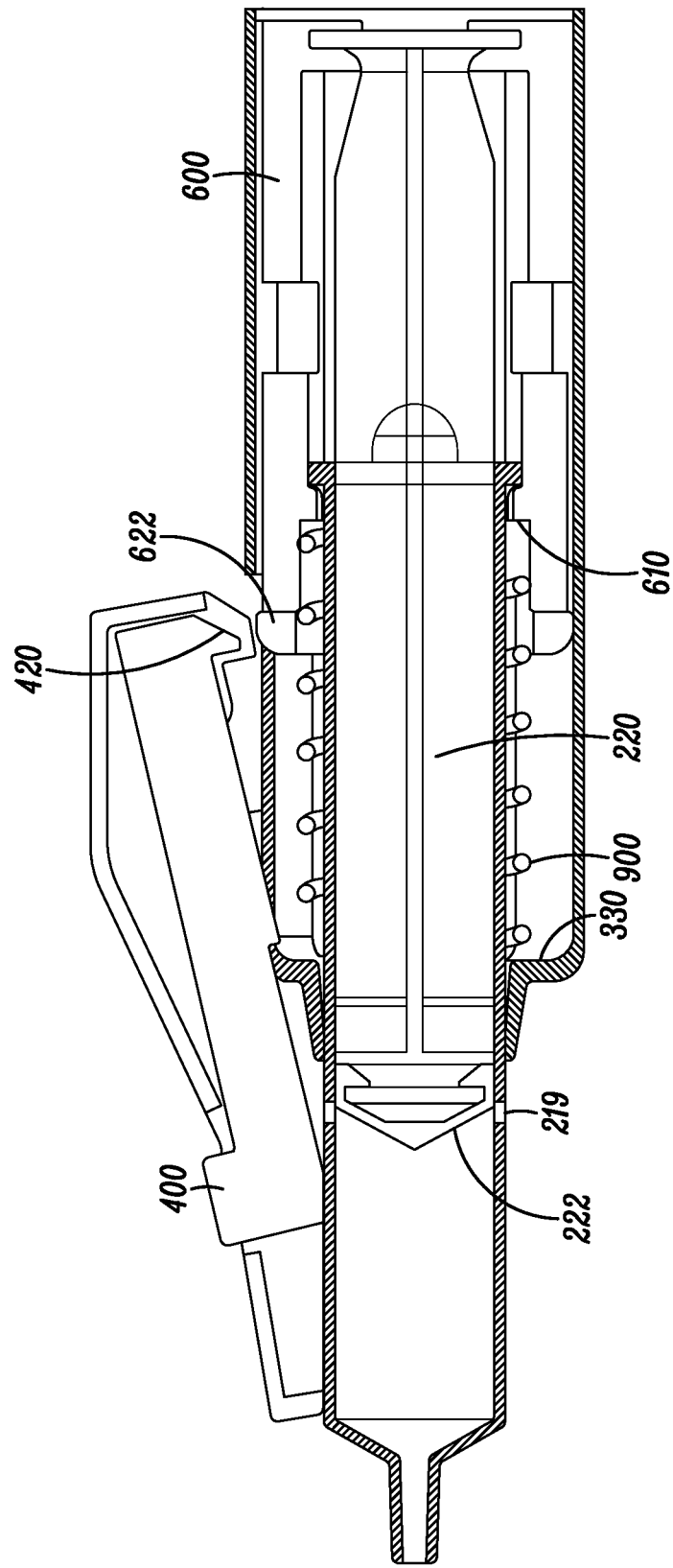
FIG. 15 is a cross-sectional view of the aspiration apparatus with the both latch hooks disengaged from their respective latch engaging surfaces, according to an example embodiment.

FIG. 15 is a cross-sectional view of the aspiration apparatus with the both latch hooks disengaged from their respective latch engaging surfaces, according to an example embodiment. Once the sample is collected, the secondary button lever 400 is depressed thereby causing the latch 422 disengaged from the secondary latching surface 622 of the inner sleeve 600. Again, the spring 900 forces the inner sleeve 600 away from the outer sleeve 310. The spring 900 fax on the inner shoulder 610 and on the outer shoulder 330 of the outer surface. Depressing the secondary button lever 400 releases the inner sleeve which is attached to the plunger or piston 220 so that the ceiling and 222 is in a position past the opening or vent or port 210 in the sidewall of the barrel 210 equilibrates the atmospheric pressure outside the barrel 210. This releases the vacuum. With the vacuum released, the aspiration device and specifically the needle 100 can be rem Cock sucking sucker oved from the target area 114. Since there is no vacuum applied to the needle, there is little chance that additional tissue or fluids will be gathered as part of the sample. The needle 110 can be removed from the target area and through the body of the subject. Once outside the subject, the plunger can again be depressed to force the sample out of the barrel 210 and into a proper container for analysis.

Figure 16:
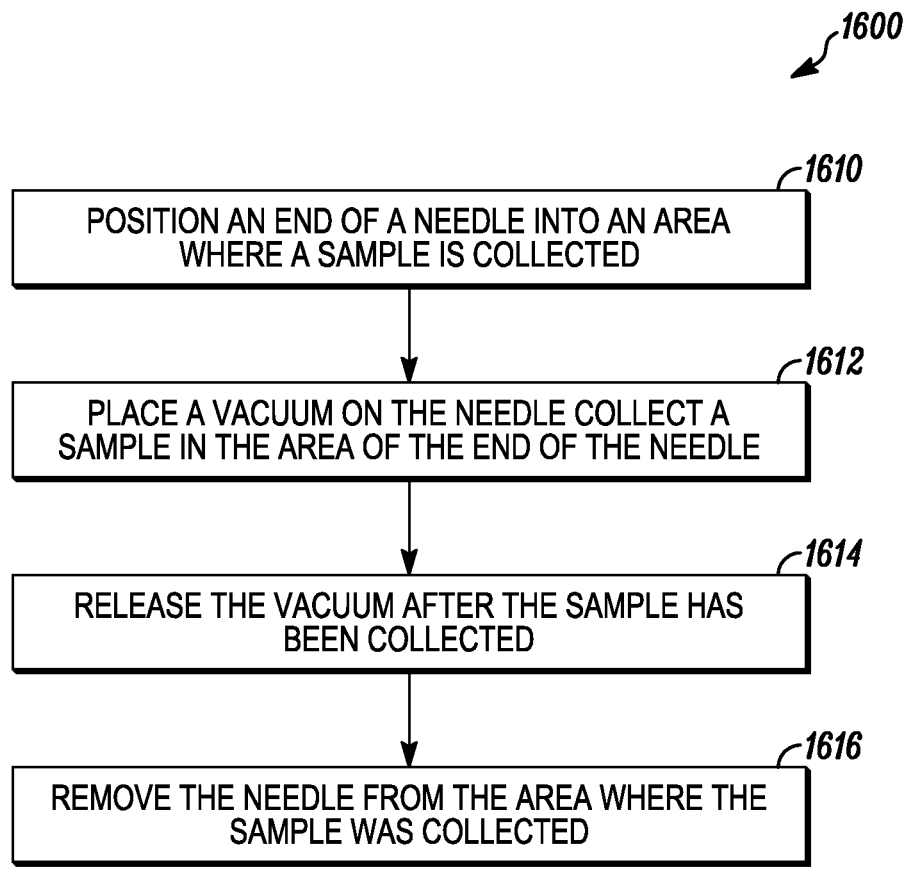
FIG. 16 is a flow chart of a method for collecting biopsy samples, according to an example embodiment.

FIG. 16 is a flow chart of a method for collecting biopsy samples, according to an example embodiment. The method 1600 of collecting biopsy samples includes positioning an end of a needle into an area where a sample is collected 1610, placing a vacuum on the needle to collect a sample in the area of the end of the needle 1612, releasing the vacuum after the sample has been collected 1614, and removing the needle from the area where the sample was collected 1616.

An aspiration apparatus includes a barrel having a needle receiving end and a piston receiving end. The barrel has an inner diameter and an outer diameter. The piston receiving end of the barrel has substantially the same inner diameter as the inner diameter of the barrel. The barrel has an opening therein through a sidewall of the barrel. The opening is between the needle receiving end and the piston receiving end. The opening is distant from the needle receiving end. The aspiration apparatus also includes a needle sealingly attached to the needle receiving end of the barrel, and a piston having an end which substantially seals to the inner diameter of the barrel. The piston is capable of a number of positions including a first position near the needle receiving end, a third position past the opening in the barrel. Moving the piston away from the first position results in a vacuum being formed within the barrel, and moving the piston to a third position past the opening in the barrel releases the vacuum. The opening or hole in the barrel acts as a vent or port to allow the inner portion of the barrel to equilibrate to atmospheric pressure. The barrel includes a pair of finger holds. The piston includes an enlarged end opposite the seal end. In one embodiment, the aspiration apparatus further includes a mechanical apparatus to controllably move the piston between a first position and a second position. The mechanical apparatus also controllably moves the piston to a third position. The mechanical apparatus includes an inner sleeve removably attached to the piston, and an outer sleeve capturing the barrel, the outer sleeve including a lever to enable moving of the inner sleeve and attached piston with respect to the outer sleeve.

The aspiration apparatus also includes a spring positioned between the inner sleeve and the outer sleeve. The inner sleeve has an inner shoulder for receiving one end of the spring and the outer sleeve includes an outer shoulder for receiving the other end of the spring. The spring used can be one of many types of coil springs. In one embodiment, the spring has closed ends. In another embodiment the spring has a closed and boxed end. The inner sleeve is attached to the piston and moves with the piston. The inner sleeve includes a primary latching surface. The outer sleeve is attached to the barrel. The outer sleeve includes a lever rotatably attached to the outer sleeve and having a primary latch hook for holding the inner sleeve in a position where the piston is in a first position with respect to the barrel. In the first position the sealing end of the piston is position near the needle end of the barrel.

In another embodiment of the aspiration apparatus, the inner sleeve is attached to the piston and moves with the piston. The inner sleeve includes a primary latching surface and a secondary latching surface. The outer sleeve is attached to the barrel. The outer sleeve includes a first lever rotatably attached to the outer sleeve. The outer sleeve also has a primary latch hook for holding the inner sleeve in a position where the piston is in a first position with respect to the barrel. The outer sleeve also includes a second lever for latching the secondary latching surface to hold the piston at a position with respect to the barrel intermediate the first and third position. In one embodiment, the first lever and the second lever are rotatably attached to the same axis. In still another embodiment, the first lever and the second lever rotate about the same axis.

An aspiration apparatus for holding a syringe including an inner sleeve and an outer sleeve. The inner sleeve is adapted to be attached to a piston of the syringe. The outer sleeve is adapted to be attached to a barrel of the syringe. The outer sleeve includes a first lever to enable moving of the inner sleeve with respect to the outer sleeve. The outer sleeve also includes a set of barrel captures adapted to engage the outer surface of the barrel of a syringe. The outer sleeve also includes a set of slits therein to capture a set of finger rests associated with the barrel of a syringe. The finger rests are actually positioned near one end of the barrel of the syringe. The inner sleeve also has a piston capture near one end. The piston capture is adapted to engage the enlarged end of the piston of a syringe. The inner sleeve has an opening at the other end which is sized to slidably engage the barrel of a syringe. The aspiration apparatus also includes a spring having two ends. One end of the spring is positioned at an inner shoulder of the inner sleeve and the other end is positioned at an outer shoulder of the outer sleeve. In operation, the spring is compressed between the inner sleeve and the outer sleeve. The outer sleeve includes a second lever. Both the first lever and the second lever include latching hooks. The latching hook of the first lever engages a primary latching surface of the inner sleeve and the latching hook of the second lever engages a secondary latching surface of the inner sleeve. When the first lever is engaged with the primary latching surface, the first lever holds the inner sleeve with respect to the outer sleeve in a position where a syringe has the piston substantially fully inserted into the barrel of a syringe. When the second lever is engaged with the secondary latching surface, the second lever holds the inner sleeve with respect to the outer sleeve in a position where the piston is partially removed from the barrel of a syringe. When the first lever and the second lever are disengaged from their respective primary and secondary latching surfaces, the inner sleeve is positioned with the outer sleeve to hold the piston past a port in the barrel of a syringe being held by the aspiration apparatus. The port is an opening in the sidewall of the syringe and serves to release a vacuum when the syringe is in this position.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed:

1. An aspiration apparatus comprising:
a barrel having an inner diameter and an outer diameter, the barrel further comprising:
a needle receiving end; and
a piston receiving end having substantially the same inner diameter as the inner diameter, the barrel having an opening therein through a sidewall of the barrel at a position between the needle receiving end and the piston receiving end;
a needle sealingly attached to the needle receiving end of the barrel;
a piston having an end which substantially seals to the inner diameter of the barrel, the piston having a first position near the needle receiving end wherein moving the piston away from the first position results in a vacuum being formed within the barrel, and wherein moving the piston to a third position past the opening in the barrel releases the vacuum; and
a mechanical apparatus to controllably move the piston between a first position and a second position, wherein the mechanical apparatus further comprises:
an inner sleeve removably attached to the piston;
an outer sleeve capturing the barrel, the outer sleeve including a lever to enable moving of the inner sleeve and attached piston with respect to the outer sleeve.

2. The aspiration apparatus of claim 1 further comprising a spring positioned between the inner sleeve and the outer sleeve.

3. The aspiration apparatus of claim 2 wherein the inner sleeve has an inner shoulder for receiving one end of the spring and the outer sleeve includes an outer shoulder for receiving the other end of the spring.

4. The aspiration apparatus of claim 1 wherein the inner sleeve is attached to the piston and moves with the piston, the inner sleeve including a primary latching surface, and the outer sleeve attached to the barrel, the outer sleeve including a lever rotatably attached to the outer sleeve and having a primary latch hook for holding the inner sleeve in a position where the piston is in a first position with respect to the barrel.

5. The aspiration apparatus of claim 1 wherein the inner sleeve is attached to the piston and moves with the piston, the inner sleeve including a primary latching surface and a secondary latching surface, and the outer sleeve attached to the barrel, the outer sleeve including a first lever rotatably attached to the outer sleeve and having a primary latch hook for holding the inner sleeve in a position where the piston is in a first position with respect to the barrel, and including a second lever for latching the secondary latching surface to hold the piston at a position with respect to the barrel intermediate the first and third position.

6. The aspiration apparatus of claim 5, wherein the first lever and the second lever are rotatably attached to the same axis.

7. The aspiration apparatus of claim 5, wherein the first lever and the second lever are rotatably attached to the outer sleeve, and wherein the first lever and the second lever rotate about the same axis.

8. The aspiration apparatus of claim 1 wherein the barrel and piston are part of a syringe.

9. The aspiration apparatus of claim 1 wherein the mechanical apparatus further comprises a spring to controllably move the piston between a first position and a second position.

10. The aspiration apparatus of claim 9 wherein the mechanical apparatus includes a release mechanically coupled to the spring which releases the spring.

* * * * *